United States Patent [19]

Lechot

[11] Patent Number: 5,658,290

[45] Date of Patent: Aug. 19, 1997

[54] ASSEMBLY COMPRISING REAMER SPINDLE AND REAMER FOR SURGERY

[75] Inventor: André Lechot, Orvin, Switzerland

[73] Assignee: Precifar S.A., La Chaux-De-Fonds, Switzerland

[21] Appl. No.: 534,101

[22] Filed: Sep. 26, 1995

[30] Foreign Application Priority Data

Sep. 28, 1994 [CH] Switzerland ................ 2 933/94

[51] Int. Cl.$^6$ .................................................. A61B 17/16
[52] U.S. Cl. .................................. 606/80; 606/84
[58] Field of Search ........................... 606/80, 79, 84

[56] References Cited

U.S. PATENT DOCUMENTS 4,621,637 11/1986 Fishbein .
5,462,548 10/1995 Pappas et al. ................. 606/80

FOREIGN PATENT DOCUMENTS 2281095 3/1976 France .

OTHER PUBLICATIONS

International Search Report No. CH 293394 dated May 18, 1995.

Primary Examiner—Michael Buiz
Assistant Examiner—Daphna Shai
Attorney, Agent, or Firm—Kane, Dalsimer, Sullivan, Kurucz, Levy, Eisele and Richard, LLP

[57] ABSTRACT

The reamer comprises a cap (1) and radial rods (2) which are arranged uniformly on the inside edge of the cap. These radial rods (2), which are at least three in number, join up at the center of the cap and are integral. The reamer spindle comprises a shank (3) on which there is fixed a reamer spindle head (5) which is equipped with a bayonet with locking means for the securing of the reamer. The securing catches (10) of the bayonet are intended to receive the radial rods (2) of the reamer. The center (14) of the bayonet is preferably recessed so that the latter can receive the radial rods (2) of the reamer and can serve as a cavity for retention of the bone substance which is removed.

3 Claims, 1 Drawing Sheet

ASSEMBLY COMPRISING REAMER SPINDLE AND REAMER FOR SURGERY

FIELD OF THE INVENTION

The invention relates to an assembly comprising reamer spindle and reamer which are intended for surgery in the field of implantation of prostheses, comprising, on the one hand, a shank to which there is fixed a reamer spindle head which is equipped with a securing device of the bayonet type equipped with locking means, and, on the other hand, a cap-shaped reamer which is equipped with radial rods which are distributed uniformly and are integral with the inside edge of the reamer and are intended to come into engagement in catches of the bayonet.

STATE OF THE ART

Such a reamer spindle/reamer assembly has already been marketed by the Applicant. In this assembly, the reamer in the shape of a hemispherical cap is equipped with three radial studs on its inside edge, which studs are intended to come into engagement in the catches of the bayonet. These latter can be locked by studs placed at the end of a slide which is movable axially on the shank of the reamer spindle and is brought against the bayonet by the action of a spring. Holes in the bayonet correspond to the studs of the slide, the studs passing through these holes in order to close the catches of the bayonet when the slide is applied against the bayonet. In order to open the catches of the bayonet, it suffices to distance the slide sufficiently from the bayonet. On account of the fact that the securing rods of the reamer are studs, the reamer has a relatively low rigidity. Moreover, since the studs have a limited length, a reamer spindle head can be used only for reamers which have clearly defined diameters situated within a narrow range, and this entails frequent assembly and disassembly of the head from the reamer spindle when using different reamers.

A reaming tool of the same type is known from the document FR No. 75 24360. This tool is intended for shaping the acetabular cavity upon replacement with a total hip joint prosthesis. It consists of a reamer which can have the shape of a hemisphere, and of a reamer spindle head which is intended to close the lower part of the reamer in such a way that the tissue particles removed during the reaming operation and arriving in the interior cavity of the reamer are held there until the end of the operation, and to be fitted on a drive shaft. According to one embodiment of this tool, a single rod fixed via its two ends to the inside of the reamer is provided for securing the reamer on the reamer spindle head. It cooperates, for example, with a securing system of the bayonet type with which the reamer spindle head is equipped. This reaming tool has good rigidity on account of the fact that, under the stresses caused by reaming, the lower edge of the reamer is pressed against the reamer spindle head, with the rod conferring on it additional stability. However, this tool presents a substantial disadvantage, namely the risk of plugging of the inside of the reamer during an operation. When plugging occurs, the reamer no longer planes down and consequently damages the bone. Another disadvantage presented by this tool is that the reamer spindle head can be used only with reamers having a clearly defined diameter, which entails, as in the case of the reamer spindle/reamer assembly already marketed by the Applicant, frequent disassembly and assembly when different reamers are used.

SUMMARY OF THE INVENTION

The object of the present invention is to provide a reamer/reamer spindle assembly by means of which it is possible to remedy the disadvantages cited above and which in particular permits the use of one reamer spindle head for all reamers having an internal diameter greater than the diameter of the reamer spindle head.

This object is achieved by the reamer spindle and reamer assembly according to the invention, characterized in that the radial rods are at least three in number and join up at the center where they are integral.

The bone substance which is detached during the reaming operation has a tendency to form a paste and thus to remain inside the reamer. Equipping the latter with a cover is not therefore necessary and is even advised against because of the risk of plugging.

The reamer spindle/reamer assembly according to the invention has, by virtue of the radial rods, good resistance to deformation, by means of which fact it is possible to obtain great precision during shaping of the desired cavity.

Since the radial rods reach from the edge of the reamer to its center, a reamer spindle head can be used with any reamer having an internal diameter greater than its own diameter. By virtue of this, the number of tools to be sterilized is reduced, which fact permits a saving in time. Since the number of reamer spindle heads is thus reduced, it is easier to be certain about their sterility or nonsterility, which fact makes it possible to reduce, or even eliminate, the risk of errors which can prove fatal for the patient being operated on.

According to a preferred variant, the bayonet is recessed at its center to a certain thickness in order to allow the radial rods thus joined to come into engagement in the catches of the bayonet without being subjected to friction in the area of their connection points. This recess also makes it possible to collect the bone substance for grafts. Thus, with the presence of connected securing rods permitting an improvement in the rigidity of the reamer and greater precision of reaming, it is still possible to collect bone substance.

BRIEF DESCRIPTION OF THE DRAWINGS

The attached drawing represents, by way of example, an embodiment of the subject of the invention.

DESCRIPTION OF THE PREFERRED EMBODIMENTS

Figure 1:
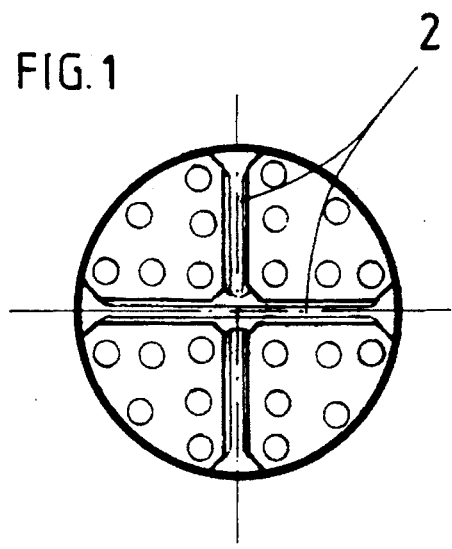
FIG. 1 is a bottom view of the reamer.
Figure 3:
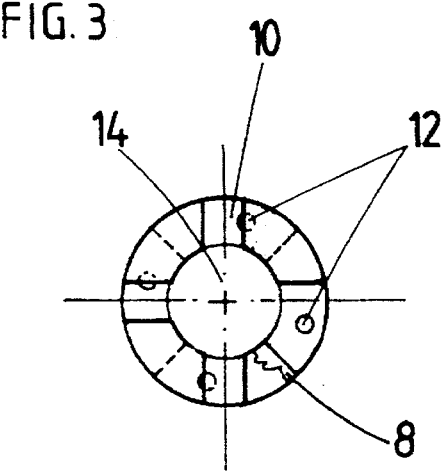
FIG. 3 represents the upper part of the reamer spindle head.
Figure 2:
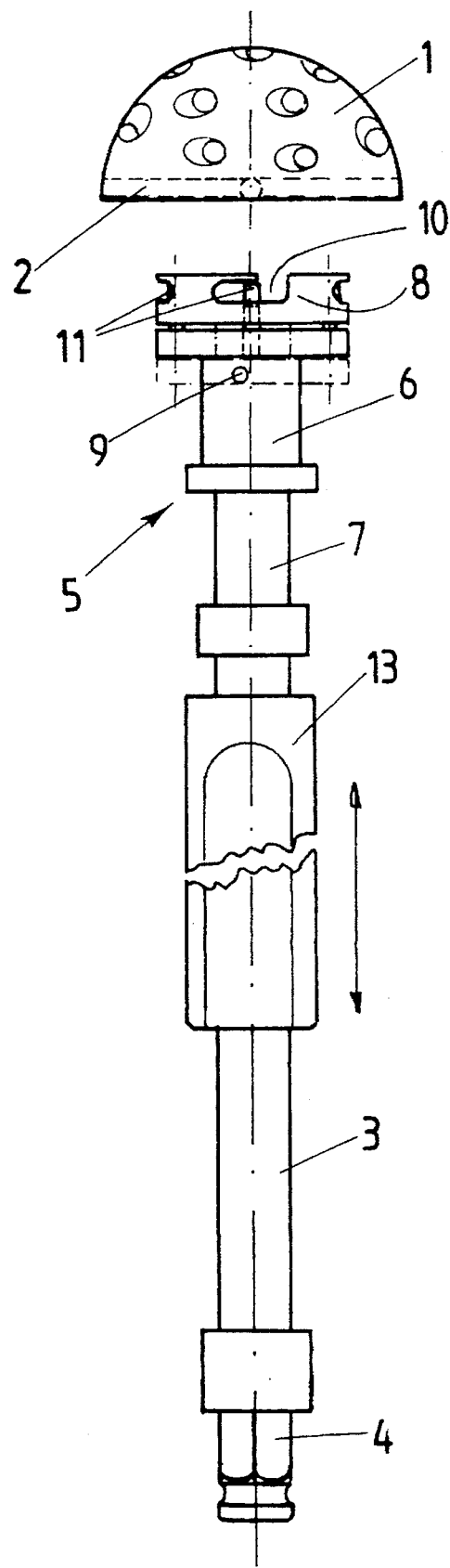
FIG. 2 represents the reamer spindle and the reamer as viewed from the side.
Figure 2:
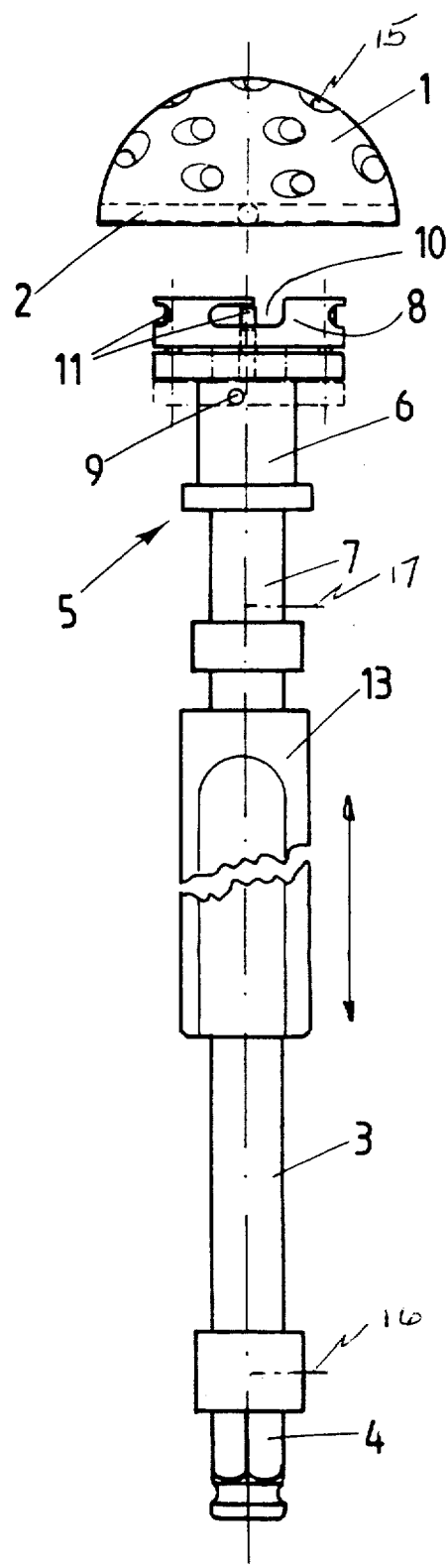

The reamer represented in FIGS. 1 and 2 consists of a hemispherical cap 1 equipped with cutting ridges 15 and with two rods 2 which are perpendicular to each other, have the length of the internal diameter of the cap 1, are welded together at the center of the cap, and whose ends are welded to the inside edges of the cap 1.

The reamer spindle represented in FIG. 2 comprises a reamer shank 3, a joining piece 4, and a reamer spindle head 5. The joining piece 4, which is used to fix the shank 3 of the reamer spindle on the machine driving it in rotation, is fixed to one of the ends of the shank 3 by a schematically illustrated screw. The head 5 of the reamer spindle is also fixed to the other end of the shank by a schematically illustrated screw 17. The head of the reamer spindle comprises a slide 6 mounted about a shaft 7, one end of which is fixed to the shank of the reamer spindle, and the other end of which is provided with a flange 8 having a diameter greater than that of the shaft 7. The slide 6 is pushed on the shaft 7 by a spring 9 which applies it against the upper flange 8 of the shaft. The flange 8 of the shaft serves as bayonet. It is recessed at its center 14 over a certain depth smaller than its thickness and thus forms a collar. Formed in this collar are four L-shaped bayonet catches 10 which are intended to receive the rods 2 of the reamer. The slide 6 is provided with four studs 11 which are parallel to the shaft 7 and to which there correspond four holes 12 in the flange 8, the studs 11 passing through these holes in order to close the catches 10 of the bayonet and thus lock the rods 2 of the reamer in the head 5 of the reamer spindle. In order to unlock the rods 2 of the reamer, it suffices to distance the slide 6 from the flange 8. As the rods 2 are then no longer blocked in the catches of the bayonet by the studs 11, the reamer can be disassembled from the reamer spindle head.

The shank 3 of the reamer spindle is equipped with a grip 13 which slides along the axis of the shank 3 of the reamer spindle.

The number of rods could be other than four, for example three or five.

The bayonet fastening could be locked in another way.

Given that one and the same reamer spindle head can be used for reamers of different diameters, the reamer spindle head could be fixed permanently to the shank.

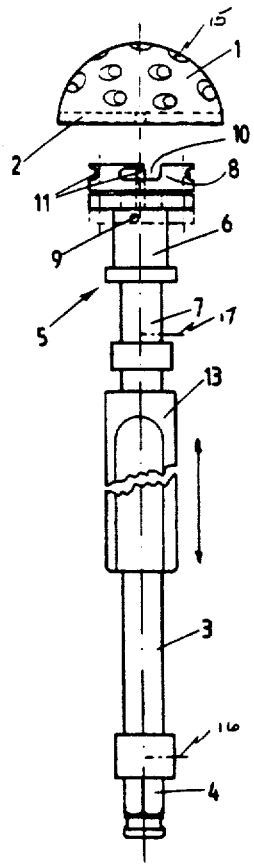

I claim:

1. Reamer spindle and reamer which are intended for surgery, comprising, on the one hand, a shank (3) to which there is fixed a reamer spindle head (5) which is equipped with a securing device of the bayonet type (10) equipped with locking means (6, 11), and, on the other hand, a cap-shaped reamer (1) which is equipped with radial rods (2) which are distributed uniformly, are integral with the inside edge of the reamer and are intended to come into engagement in catches (10) of the bayonet, characterized in that the radial rods (2) are at least three in number and join up at the center of the cap where they are integral.

2. Reamer spindle and reamer according to claim 1, characterized in that the bayonet is in the form of a collar whose center (14) is recessed to a certain thickness in order to be able to receive the radial rods (2) of the reamer, reducing the friction in the area of their connection point.

3. Reamer spindle and reamer according to claim 2, characterized in that the radial rods of the reamer are four in number.

* * * * *

UNITED STATES PATENT AND TRADEMARK OFFICE
CERTIFICATE OF CORRECTION

PATENT NO. : 5,658,290
DATED : August 19, 1997
INVENTOR(S) : Andre Lechot

It is certified that error appears in the above-identified patent and that said Letters Patent is hereby corrected as shown below:

The title page, showing an illustrative figure, should be deleted and substitute therefor the attached title page.

Delete Figure 2 and substitute the attached Figure 2.

Column 2, line 62, after "screw", insert --16--.

Signed and Sealed this

Sixth Day of January, 1998

*Attest:*

*Attesting Officer*

BRUCE LEHMAN

*Commissioner of Patents and Trademarks*

United States Patent [19]

Lechot

[11] Patent Number: 5,658,290
[45] Date of Patent: Aug. 19, 1997

[54] ASSEMBLY COMPRISING REAMER SPINDLE AND REAMER FOR SURGERY

[75] Inventor: André Lechot, Orvin, Switzerland

[73] Assignee: Precifar S.A., La Chaux-De-Fonds, Switzerland

[21] Appl. No.: 534,101

[22] Filed: Sep. 26, 1995

[30] Foreign Application Priority Data

Sep. 28, 1994 [CH] Switzerland ............ 2 933/94

[51] Int. Cl.$^6$ .................................. A61B 17/16
[52] U.S. Cl. ............................ 606/80; 606/84
[58] Field of Search .................. 606/80, 79, 84

[56] References Cited

U.S. PATENT DOCUMENTS 4,621,637 11/1986 Fishbein .
5,462,548 10/1995 Pappas et al. ................. 606/80

FOREIGN PATENT DOCUMENTS 2281095  3/1976  France .

OTHER PUBLICATIONS

International Search Report No. CH 293394 dated May 18, 1995.

Primary Examiner—Michael Buiz
Assistant Examiner—Daphna Shai
Attorney, Agent, or Firm—Kane, Dalsimer, Sullivan, Kurucz, Levy, Eisele and Richard, LLP

[57] ABSTRACT

The reamer comprises a cap (1) and radial rods (2) which are arranged uniformly on the inside edge of the cap. These radial rods (2), which are at least three in number, join up at the center of the cap and are integral. The reamer spindle comprises a shank (3) on which there is fixed a reamer spindle head (5) which is equipped with a bayonet with locking means for the securing of the reamer. The securing catches (10) of the bayonet are intended to receive the radial rods (2) of the reamer. The center (14) of the bayonet is preferably recessed so that the latter can receive the radial rods (2) of the reamer and can serve as a cavity for retention of the bone substance which is removed.

3 Claims, 1 Drawing Sheet